United States Patent [19]
Bonham

[11] Patent Number: 5,847,133
[45] Date of Patent: Dec. 8, 1998

[54] IONIC HALOMETHYL-1,3,5-TRIAZINE PHOTOINITIATORS

[75] Inventor: James Alan Bonham, Lake Elmo, Minn.

[73] Assignee: Minnesota Mining and Manufacturing Company, St. Paul, Minn.

[21] Appl. No.: 862,809

[22] Filed: May 23, 1997

[51] Int. Cl.$^6$ .................................................. C07D 251/22
[52] U.S. Cl. .............................................................. 544/216
[58] Field of Search ............................................. 544/216

[56] References Cited

U.S. PATENT DOCUMENTS

| | | | |
|---|---|---|---|
| 3,495,987 | 2/1970 | Moore | 546/153 |
| 3,617,288 | 11/1971 | Hartman et al. | 564/305 |
| 3,640,718 | 2/1972 | Smith | 96/89 |
| 3,954,475 | 5/1976 | Bonham et al. | 430/281 |
| 3,987,037 | 10/1976 | Bonham et al. | 546/180 |
| 4,189,323 | 2/1980 | Buhr | 430/281 |
| 4,239,850 | 12/1980 | Kita | 430/281 |
| 4,259,432 | 3/1981 | Kondoh et al. | 430/281 |
| 4,505,793 | 3/1985 | Tamoto et al. | 204/159.16 |
| 4,696,888 | 9/1987 | Buhr | 430/270 |
| 4,772,534 | 9/1988 | Kawamura et al. | 430/176 |
| 4,826,753 | 5/1989 | Higashi et al. | 430/281 |
| 4,837,128 | 6/1989 | Kawamura et al. | 430/281 |
| 4,997,745 | 3/1991 | Kawamura et al. | 430/281 |
| 5,034,526 | 7/1991 | Bonham et al. | 544/209 |
| 5,116,977 | 5/1992 | Rossman et al. | 544/113 |
| 5,310,618 | 5/1994 | Kawamura | 430/157 |
| 5,455,143 | 10/1995 | Ali | 430/281 |
| 5,484,919 | 1/1996 | Bonham | 544/193.1 |
| 5,489,499 | 2/1996 | Yumoto | 430/281.1 |
| 5,496,504 | 3/1996 | Bonham et al. | 252/600 |

FOREIGN PATENT DOCUMENTS 63-298339  12/1988  Japan.

*Primary Examiner*—Yogendra N. Gupta

[57] ABSTRACT

Novel water-soluble triazine photoinitiators and bifunctional ionic photoinitiators having an anion containing a photo-labile halomethyl-1,3,5-triazine and a photoinitiator cation are described. The ionic compounds are good photoinitiators for initiating free radical and acid sensitive reactions. The ionic photoinitiators are easily synthesized and eliminate the need for a combination of photoinitiators in a photocurable, photopolymerizable, or photoacid sensitive composition. Additionally, the radiation-sensitive compounds are resistant to migration in photosensitive compositions. The ionic photoinitiators are particularly useful in compositions for use in printing, duplication, copying, and other imaging systems.

11 Claims, No Drawings

IONIC HALOMETHYL-1,3,5-TRIAZINE PHOTOINITIATORS

FIELD OF THE INVENTION

This invention relates to photosensitive ionic photoinitiators, more particularly, to water-soluble halomethyl,1,3,5-triazine compounds and ionic salt derivatives of anionic halomethyl,1,3,5-triazine compounds with cationic radiation-sensitive compounds.

BACKGROUND OF THE INVENTION

Compounds that decompose upon exposure to actinic radiation are useful in the graphic arts and are commonly referred to as photoinitiators. They are typically used for in-situ photochemical production of free radical species or acidic species which are subsequently used to initiate free radical catalyzed or acid catalyzed polymerizations, or to react with acid sensitive compounds. General reviews of photoinitiator compounds and photoinitiated processes are described in C. G. Roffey, *Photopolymerization of Surface Coatings,* John Wiley and Sons (New York, 1982), Chapters 1, 3, and 4; and in *UV Curing: Science and Technology,* Volume II, Chapter 1 edited by S. Peter Papas. Technology Marketing Corporation (Stamford, Conn. 1985).

Halomethyl-1,3,5-triazines are a class of free radical photoinitiators having particularly useful characteristics. They are employed in compositions to produce free radicals for (1) initiating polymerization or color changes and/or (2) initiating secondary reactions upon liberation of acid by the interaction between the halogen free radicals produced with hydrogen donors. The sensitivity of halomethyl-1,3,5-triazines to actinic radiation of a particular range can be achieved by the incorporation of sensitizing dyes including cyanine dyes, carbocyanine dyes, acridines, polycyclic aromatic hydrocarbons, ketocoumarins, and amino-substituted chalcones. U.S. Pat. Nos. 3,495,987; 3,640,718; 3,617,288; 4,259,432; 4,505,793; 4,239,850; 4,997,745; and 5,455,143 provide examples of compositions containing various combinations of sensitizers and halomethyl-1,3,5-triazines.

Chromophore-substituted halomethyl-1,3,5-triazines are a particularly useful class of photopolymerization initiators since they can be designed to respond to radiation in the near ultraviolet (UV) to the visible light region. U.S. Pat. Nos. 3,987,037; 3,954,475; 4,189,323; 4,696,888; 4,772,534; 4,826,753; 4,837,128; 5,484,919; and 5,489,499 provide examples of chromophore-substituted halomethyl-1,3,5-triazine compounds that are photoactivated by irradiation to light within the near UV to Visible range. JP 63-298339 describes a water-soluble phenyl substituted s-triazine compound which is useful as a free radical photoinitiator.

Bifunctional triazine photoinitators are also known which have a photolabile halomethyl-1,3,5-triazine moiety covalently bonded to an amine moiety, a sensitizer moiety, a monomer moiety, or another photoinitiator. U.S. Pat. No. 5,116,977 discloses compounds having a halomethyl-1,3,5-triazine moiety and at least one amine-containing moiety covalently bonded within one molecule. U.S. Pat. Nos. 5,034,526 and 5,310,618 disclose compounds having a halomethyl-1,3,5-triazine moiety and at least one sensitizer moiety covalently bonded within one molecule. U.S. Pat. No. 5,496,504 discloses compounds having a halomethyl-1,3,5-triazine moiety and at least one monomeric moiety covalently bonded within one molecule.

U.S. Pat. No. 5,116,977 discloses bifunctional compounds having a halomethyl-1,3,5-triazine moiety and at least one photoinitiator moiety within one molecule. These bifunctional triazine compounds require that both the photoinitiator and triazine moieties be joined by covalent bonds. The synthetic procedures used in their preparation can be complicated and are limited by interfering reactions. Reaction conditions must be avoided which will cause decomposition products and low yields. Thus, extensive experimentation is required to devise synthetic methods of combining the moieties into the same molecule.

SUMMARY OF THE INVENTION

The present invention provides an ionic bifunctional photoinitiator having the general formula $P^+T^-$ wherein $P^+$ is a radiation-sensitive organic cation and $T^-$ is a halomethyl-1,3,5-triazine anion. The radiation-sensitive organic cation is selected from radiation-sensitive "onium" cations such as diazonium cations, iodonium cations, sulfonium cations, selenonium cations, arsonium cations, ammonium cations, and phosphonium cations; and radiation-sensitive compounds substituted with a cationic group, such as benzoins, benzoin alkyl ethers, quinones, bis-imidazoles, acetophenones, or benzophenones substituted with a cationic group, such as a quaternary ammonium group or a quaternary phosphonium group. The halomethyl-1,3,5-triazine anion is selected from halomethyl-1,3,5-triazine compounds substituted with a anionic group, such as a carboxyl anion ($-CO_2^-$), a sulfonate anion ($-SO_3^-$), or a phosphonate anion ($-PO_3^-$).

The ionic bifunctional photoinitiators are easily prepared in high yield by an ion-exchange reaction of salts of the radiation-sensitive cation and the halomethyl-1,3,5-triazine anion. The reaction conditions are mild and the reaction solvent may be selected such that the organic salt compound of the invention precipitates upon formation or is precipitated upon the addition of a non-solvent.

In another embodiment of the present invention, a water-soluble or dispersible, chromphore-substituted halomethyl-1,3,5-triazine compound is provided having at least one halomethyl-substitutent attached to a carbon atom of the triazine nucleus; and at least one styryl substituent attached to a second carbon atom of the traizine nucleus; and at least one pendent acid group linked to the phenyl group of the styryl substituent by a covalent bond or by a linking group, or to a third carbon atom of the triazine nucleus by a linking group.

Preferred water-soluble or dispersible, chromophore-substituted halomethyl-1,3,5-traizine photoinitiator compounds are represented by the following general structure:

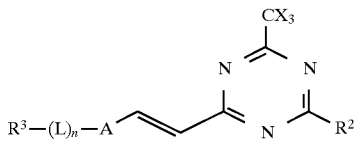

wherein X is a chlorine or a bromine atom; A is an aryl group having 1 to 3 rings; L is a linking group selected from the group consisting of carbamato, carbamido, amino, amido, alkyl having up to 15 carbon atoms, alkenyl, alkynyl, keto, ester, sulfonyl, aryl, and combinations thereof; n is 0 or 1; $R^3$ is an acid group selected from the group consisting of sulfonic acid ($-SO_3H$), phosphonic acid ($-PO_3H$) and salts thereof; and $R^2$ is $-CX_3$, $-NH_2$, NHR, $-NR_2$, $-OR$, or $-R$, where R is an alkyl group having up to 15 carbon atoms, an aryl group having up to three rings, or a heterocyclic aromatic group, or combinations thereof.

In another embodiment of the present invention, a photopolymerizable composition is provided comprising (a)

either the water-soluble triazine photoinitiator or the ionic bifunctional photoinitiator described above and (b) an unsaturated, free-radical initiated, chain propagating addition polymerizable compound or acid sensitive polymerizable compound. The photopolymerizable composition may additionally contain an acid sensitive color-forming or bleachable dye; or a photooxidizable leuco dye.

In another embodiment of the present invention, a photosensitive element is provided comprising a substrate having deposited thereon the photopolymerizable composition described above.

In yet another embodiment of the present invention, a photosensitive element is provided comprising a substrate having deposited thereon a composition comprising either the water-soluble triazine photoinitiator or the ionic bifunctional photoinitiator described above and an acid degradable compound.

As used herein, the phrase "organic salt" refers to an ionic compound formed from an organic cation and an organic anion.

"Metal salt" refers to an ionic compound formed from a metal cation (i.e., alkali metal ions, etc.) and an organic anion.

"Water-soluble" refers to materials that are soluble or dispersible in water. In other words, the materials are held in suspension or form a homogeneous solution in water.

"Radiation-sensitive cation" refers to a cationic organic compound that is sensitive to actinic radiation, either directly or in combination with a sensitizer; and forms an ionic bond with a halomethyl-1,3,5-triazine anion.

"Halomethyl-1,3,5-triazine anion" refers to an anionic organic compound having a 1,3,5-triazine nucleus with at least one trihalomethyl group (preferably a trichloromethyl ($-CCl_3$) group or a tribromomethyl ($-CBr_3$) group) covalently attached to a carbon atom of the triazine nucleus; and a linking group covalently attached to both a different carbon atom of the triazine nucleus and an anionic group. The anionic group forms an ionic bond with the radiation-sensitive cation.

"Chromophore-substituted" refers to a group capable of selective light absorption which imparts color to the compound.

Within the field of organic chemistry and particularly within the field of organic photoinitiators, it is widely understood that significant substitution of compounds is tolerated or even useful. In the present invention, for example, the term aryl group allows for substitutents which is a classic alkyl, such as methyl, ethyl, propyl, hexyl, isooctyl, dodecyl, stearyl, etc. The term group specifically envisions and allows for substitutions on alkyls which are common in the art, such as hydroxy, halogen, nitro, cyano, alkoxy, carbonyl, keto, ester, carbamato, etc., as well as including an unsubstituted alkyl moiety. The particular identity of the substituents is not critical. However, the substituents should be selected so as to not adversely affect the photoinitiation characteristics or light sensitivity or adversely interfere with the formation of the ionic bifunctional photoinitiator of the present invention.

DETAILED DESCRIPTION OF THE INVENTION

The present invention provides water soluble triazine photoinitiators having pendant acidic groups or salts thereof and ionic compounds which are organic salts of a radiation-sensitive cation and a halomethyl-1,3,5-triazine anion referred to herein as ionic bifunctional photoinitiators having the following general formula:

$$P^+ \ T^-$$

wherein; $P^+$ represents a radiation-sensitive cation, and $T^-$ represents a halomethyl-1,3,5-triazine anion.

Radiation-sensitive cations represented by $P^+$ include radiation-sensitive "onium" cations, such as aryldiazonium cations, aryliodonium cations, arylsulfonium cations, diarylalkylsulfonium cations, dialkylaryl sulfonium cations, dialkylphenacylsulfonium cations, triarylselenonium cations, and triarylarsonium cations; and photoinitiators, such as benzoins, benzoin alkyl ethers, quinones, bisimidazoles, acridines, thioxanthones, acetophenones, and benzophenones, which are substituted with a cationic group (i.e., a quaternary ammonium group or a quaternary phosphonium group).

Halomethyl-1,3,5-triazine anions represented by $T^-$ include halomethyl-1,3,5-triazine anions that are capable of forming an organic salt, such as halomethyl-1,3,5-triazines having at least one trichloromethyl ($-CCl_3$) group or a tribromomethyl ($-CBr_3$) group directly attached to a carbon atom of the triazine nucleus; and a linking group which provides a means of covalently attaching a pendant anionic group to the triazine nucleus. Suitable anionic groups include carboxylate groups ($-CO_2^-$), sulfonate groups ($-SO_3^-$), and phosphonate groups ($-PO_3^-$).

Radiation-sensitive cations where $P^+$ is a monofunctional aryldiazonium cation include organic cations, such as 4-diazodiphenylamine, 3-methoxy-4-diazodiphenylamine, 2-methoxy-4-diazodiphenylamine, 4'-methoxy-4-diazodiphenylamine, and 4-diazodiphenyl ether. Radiation-sensitive cations where $P^+$ is a multifunctional diazonium cation include diazonium resins, such as those prepared by the condensation of an aryl diazonium cation and an active carbonyl compound (i.e., formaldehyde, acetaldehyde, benzaldehyde, acetone, and glyoxylic acid). Other suitable compounds that can be condensed with diazonium cations include 4,4'-bis(hydroxymethyl)diphenyl ether; 4,4'-bis (methoxymethyl)diphenyl ether; 4,4'-bis(methoxymethyl) diphenyl methane; and 4,4'-bis(acetoxymethyl) diphenylsulfone. Examples of diazonium monomers and multifunctional diazonium condensation resins which may be used in the preparation of ionic bifunctional photoinitiators ($P^+ \ T^-$) are disclosed in U.S Pat. Nos. 2,714,066; 3,867,147; 4,436,804; 5,112,743; 5,308,735; and 5,459,011 incorporated herein by reference. Other useful multifunctional diazonium cations are based on polymers having pendent diazonium groups and are described in U.S. Pat. Nos. 4,284,705; 4,581,313; 4,902,601; and 5,466,789 incorporated herein by reference.

Radiation-sensitive cations where $P^+$ is an iodonium cation include diaryliodonium cations which are symmetrically substituted with the same aryl group or unsymmetrically substituted with disimilar aryl groups. Suitable diaryliodonium cations include diphenyliodonium, ditolyliodonium, di(4-chlorophenyl)iodonium, di(4-acetylphenyl)iodonium, di(carbomethoxyphenyl)iodonium, di(4-phenylphenyl)iodonium, tolylphenyliodonium, di(dodecylphenyl)iodonium, (4-trifluoromethylphenyl) phenyliodonium, (4-octadecyloxyphenyl)phenyliodonium, (3-benzoylphenyl)phenyliodonium, and 3,7-di-t-butyl-10H-dibenzo[β,ε]iodonium. Examples of diaryliodonium cations and compounds which may be used in the preparation of ionic bifunctional photoinitiators ($P^+ \ T^-$) are described in U.S. Pat. Nos. 3,729,313; 3,981,897; 4,076,705; 4,386,154; 4,529,490; 5,079,378; and 5,488,147 incorporated herein by reference.

Radiation-sensitive cations where $P^+$ is a sulfonium cation include triarylsulfonium cations which are symmetrically substituted with the same aryl group; or unsymmetrically substituted with dissimilar aryl groups; or unsymmetrically substituted with a combination of aryl, aralkyl, or alkyl groups. Suitable sulfonium cations include triphenylsulfonium, diphenylmethylsulfonium, phenylmethylbenzylsulfonium, dimethylphenylsulfonium, diphenylnaphthylsulfonium, (4-butoxyphenyl)diphenylsulfonium, tris(4-phenoxyphenyl)sulfonium, 4-[N-(methacryloylethyl)-carbamoyl]phenyldimethylsulfonium, (4-thiopheneyl)diphenylsulfonium, 10-methylphenoxanthenium, 4-cyanobenzyl-2-[5-naphthacenyl]methylsulfonium, 2,5-[bis-2-phenylmethyl-p-cyanobenzylsulfonium]anisole, and 5,12-[bis-2-phenylmethyl-3,5-bis-trifluoromethylbenzylsulfonium] naphthacene. Examples of sulfonium cations and sulfonium compounds which may be used in the preparation of ionic bifunctional photoinitiators ($P^+ T^-$) are disclosed in U.S. Pat. Nos. 4,069,054; 4,250,053; 4,529,490; 5,079,378; 5,089,374; and 5,101,053 incorporated herein by reference. Other useful cations are disclosed in EP 0455083; EP 0473547; DE 4305332; and WO 91/06039 incorporated herein by reference.

Radiation-sensitive organic cations where $P^+$ is a selenonium, arsonium, ammonium, or phosphonium cation may also be used in the preparation of ionic bifunctional photoinitiators ($P^+ T^-$). Representative examples of these cations are described in U.S. Pat. No. 5,089,374 and WO 91/06039 incorporated herein by reference. Suitable selenonium cations include triphenylselenonium, and (4-t-butylphenyl)diphenylselenonium. Examples of quaternary ammonium salts which photodissociate to give tertiary amines, such as trimethylbenzhydryl ammonium cations, and 1,4-difluorenyldiazabicyclooctane.

Suitable radiation-sensitive organic cations ($P^+$) can also include photoinitiators such as benzoin, benzoin alkyl ether, quinone, bisimidazole, acridine, thioxanthone, acetophenone, or benzophenone compounds, which are substituted with a cationic group, such as a quaternary ammonium group or a quaternary phosphonium group. The purpose of the cationic group is to provide an ionic bonding site for forming an organic salt with the halomethyl-1,3,5-triazine anion. The only limitation of the cationic group is that it does not destroy the photosensitivity of the photoinitiator moiety. A preferred cationic group is a quaternary ammonium group and in most cases is not directly attached to the photoinitiator moiety but is attached as a remote substituent. The quaternary nitrogen can be substituted with alkyl groups, aralkyl groups, aryl groups, or a combination thereof. The quaternary nitrogen may also be a derivative of an heterocyclic ring nitrogen, such as piperidine, or heterocyclic aromatic ring, such as pyridine. A preferred method for the preparation of a radiation-sensitive cation of this type is to prepare an intermediate derivative of the photoinitiator onto which the quaternary ammonium cation is formed or attached by covalent bonds. Many different synthetic pathways could be envisioned by those skilled in the art. For example, one method of forming a quaternary ammonium cation is by exhaustive alkylation of an amine nitrogen using an alkylating reagent, such as an alkyl halide or dimethylsulfate. Alternatively, a convenient method of attaching a quaternary amine to a photoinitiator is by the reaction of a hydroxyl group with glycidyl tetramethylammonium chloride to attach a 2-hydroxy-N,N,N-trimethylpropanaminium cation. Representative examples of thioxanthone cation photoinitiators having a quaternary ammonium group prepared by this method are described in U.S. Pat. No. 4,791,213, incorporated herein by reference, and include compounds, such as 2-hydroxy-3-(9-oxo-9H-thioxanthen-4-yloxy)-N,N,N-trimethylpropanaminium, and 2-hydroxy-3-(1-methyl-9-oxo-9H-thioxanthen-4-yloxy)-N,N,N-trimethylpropanaminium. Representative examples of benzophenone cation photoinitiators having a quaternary ammonium group are described in EP 0279475, incorporated herein by reference, and include compounds, such as 2-hydroxy-3-(4-benzoylphenoxy)-N,N,N-trimethyl-1-propanaminium, and 2-hydroxy-3-(2-benzoyl-5-methoxyphenoxy)-N,N,N-trimethyl-1-propanaminium. One could reasonably extrapolate these procedures for preparing compounds to all classes of photoinitiators having quaternary ammonium groups attached thereon.

Other photoinitiators that can be derivatized with quaternary ammonium or phosphonium cations to form radiation-sensitive cations ($P^+$) include the 2,4,5-triarylimidazolyl dimers (i.e., 2,4,5-triphenylimidazolyl dimer); or quinones (i.e., anthraquinone); benzoin and benzoin alkyl ethers (i.e., benzoin methyl ether); acetophenones (i.e., α,α-diethoxyacetophenone); and α-aminoketones (i.e., 2-methyl-1-[4-methylthiophenyl]-2-morpholino-propan-1-one). A variety of useful photoinitiator classes are described in C. G. Roffey, *Photopolymerization of Surface Coatings*, John Wiley and Sons (New York, 1982), Chapters 1, 3, and 4; and in *UV Curing: Science and Technology*, Volumes I and II edited by S. Peter Papas, Technology Marketing Corporation (Stamford, Conn.).

Representative examples of halomethyl-1,3,5-triazine anions ($T^-$) include halomethyl-1-3-5-triazine compounds capable of forming an organic salt having at least one trihalomethyl group (i.e., trichloromethyl (—$CCl_3$) group or a tribromomehyl (—$CBr_3$) group) directly attached to a carbon atom of the triazine nucleus; and a linking group which provides a means of covalently attaching a pendant anionic group to the triazine nucleus. Suitable anionic groups include carboxyl anions (—$CO_2^-$), sulfonate anions (—$SO_3^-$), and phosphonate anions (—$PO_3^-$). The exact identity of the linking group is not critical, but it should be selected such that it does not interfere with organic salt formation or adversely affect the light sensitivity of the compound. Suitable linking groups include carbamato (—$NHCO_2$—); carbamido (—NHCONH—); amino (—NH—); amido (—CONH—); alkyl (i.e., having up to 15 carbon atoms); oxy (—O—); alkenyl (—C=C—); alkynyl (—C≡C—); keto (—CO—); ester (—$CO_2$—); sulfonyl (—$SO_2$—); aryl, (i.e., phenyl, naphthyl, and anthranyl); and combinations thereof.

Halomethyl-1,3,5-triazine compounds having linking groups with pendant anionic groups comprising an aromatic or aliphatic carboxylic acid group or its carboxylate salt are useful as water soluble photoinitiators and are particularly useful in the preparation of halomethyl-1,3,5-triazine anion ($T^-$). The carboxylic acid or carboxylate group can be linked to the halomethyl triazine moiety by many different groups and its purpose is to form the organic salt with the cationic photoinitiator. A wide variety of halomethyl-1,3,5-triazines having carboxylic acid groups are described in U.S. Pat. Nos. 4,772,534; 4,826,753; and 5,489,499; incorporated herein by reference. These triazine compounds are useful in the preparation of ionic bifunctional photoinitiators ($P^+ T^-$).

Other examples of chromophore-substituted triazine moieties are described in U.S. Pat. Nos. 3,987,037; 4,476,215; 4,619,998; 4,696,888; 4,189,323; and 4,837,128; incorporated herein by reference.

Halomethyl-1,3,5-triazines having an aromatic or aliphatic sulfonic acid group or its sulfonate salt are particularly useful as water soluble triazine photoinitiators and are also useful in the preparation of ionic bifunctional photoinitiators (P$^+$ T$^-$). Chromophore-substituted halomethyl-1,3,5-triazines of the present invention having the general formula 1 are particularly useful as water soluble triazine photoinitiators and are also useful in the preparation of ionic bifunctional photoinitiators (P$^+$T$^-$).

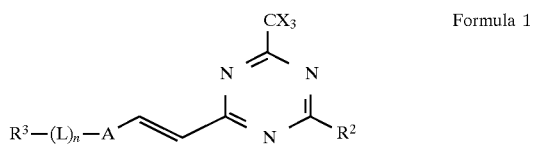

Formula 1 wherein X is a chlorine or a bromine atom; A is an aryl group having 1 to 3 rings; L is a linking group selected from the group consisting of carbamato, carbamido, amino, amido, alkyl having up to 15 carbon atoms, alkenyl, alkynyl, keto, ester, sulfonyl, aryl, and combinations thereof; n is 0 or 1; R$^3$ is an acid group selected from the group consisting of sulfonic acid (—SO$_3$H), phosphonic acid (—PO$_3$H) and salts thereof; and R$^2$ is —CX$_3$, —NH$_2$, NHR, —NR$_2$, —OR, or —R, where R is an alkyl group having up to 15 carbon atoms, an aryl group having up to three rings, or a heterocyclic aromatic group, or combinations thereof.

A preferred water-soluble halomethyl-1,3,5-triazine photoinitiators having an aromatic sulfonic acid group is represented by the general Formula 2. Reaction I depicts one possible synthetic route for the preparation of a water soluble halomethyl-1,3,5-triazine compound having Formula 2. The triazine compound having Formula 2 may be further modified to form a bifunctional photoinitiator (P$^+$ T$^-$) where T$^-$ is the acid anion of Formula 2.

Ortho, meta and para derivatives of the sulfonic acid-substituted triazine compound of Formula 2 are preferred. These esters are easily prepared by reaction of a hydroxyl derivative of the triazine with 2-sulfobenzoic anhydride. Although these compounds possess a high molecular weight, they exhibit remarkable water solubility and possess an amphipathic structure typical of sulfonate surfactants, i.e., they are composed of groups of opposing solubility tendencies. The meta-substituted compound, for example, has a molecular weight of 652 and will dissolve in water at a concentration of 10% or more. The higher molecular weight provides the advantage of preventing undesirable migration of the triazine materials into adjacent layers. They are also soluble in a wide selection organic solvents including alcohols, ketones, aromatic hydrocarbons, esters, chlorinated hydrocarbons, esters, and ethers. In addition, the compounds are soluble in common aqueous developers used in photoresist, printing plate and color proofing applications.

Other examples of halomethyl-1,3,5-triazines having a sulfonate group useful for the preparation of ionic bifunctional phototinitiators (P$^+$ T$^-$) are described in JP 63-298339 and are listed in Table I below.

TABLE I

| R$_1$ | R$_2$ | R$_3$ |
|---|---|---|
| —SO$_3$$^-$Na$^+$ | —H | —H |
| —CO$_2$$^-$Na$^+$ | —H | —H |
| —COCH$_3$ | —SO$_3$$^-$Na$^+$ | —H |
| —OCH$_3$ | —SO$_3$$^-$Na$^+$ | —H |
| —N(CH$_2$CO$_2$C$_2$H$_5$)$_2$ | —SO$_3$$^-$Na$^+$ | —H |
| —N(CH$_2$CH$_2$Cl)$_2$ | —SO$_3$$^-$Na$^+$ | —H |

Reaction I

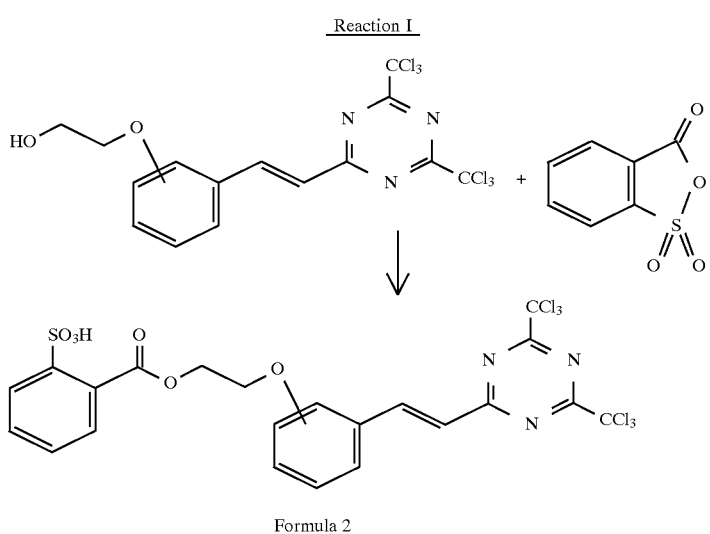

Formula 2

TABLE I-continued

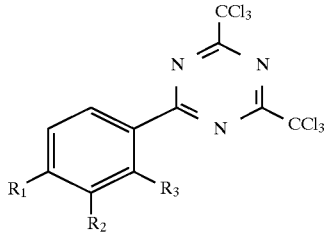

| R₁ | R₂ | R₃ |
|---|---|---|
| —C₆H₅-p-SO₃⁻Na⁺ | —H | —CH₃ |
| 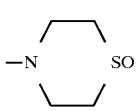 | —SO₃⁻Na⁺ | —H |

The preferred reaction method for the preparation of compounds P⁺ T⁻ is a simple ion exchange. A salt solution of the radiation sensitive cation is reacted with a salt solution of the halomethyl,1,3,5-triazine anion or its acid as illustrated in Reaction II.

Reaction II

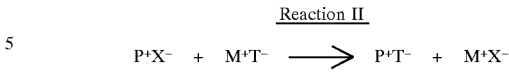

wherein X⁻ represents an inorganic anion or an organic anion, and M⁺ represents a proton, an organic cation, or an alkali metal cation. Various reaction solvents can be used including water, alcohols, esters, amides, lactones, ethers, chlorinated hydrocarbons, aromatic hydrocarbons, and ketones. The solvent for the salt solution of the radiation-sensitive cation may be the same or different from the solvent used for the salt solution of the halomethyl,1,3,5-triazine anion or its acid. The most preferred method is to select a solvent or combination of solvents in which the starting materials are soluble, but the reaction product selectively precipitates. However, it is also possible to isolate the product by the addition of a nonsolvent which will cause selective precipitation of either reaction product. The reaction is simple, economical, and can performed at room temperature.

Representative examples of radiation-sensitive cations (P⁺) which may be used to produce ionic bifunctional photoinitiators (P⁺ T⁻) are listed in Table II.

TABLE II

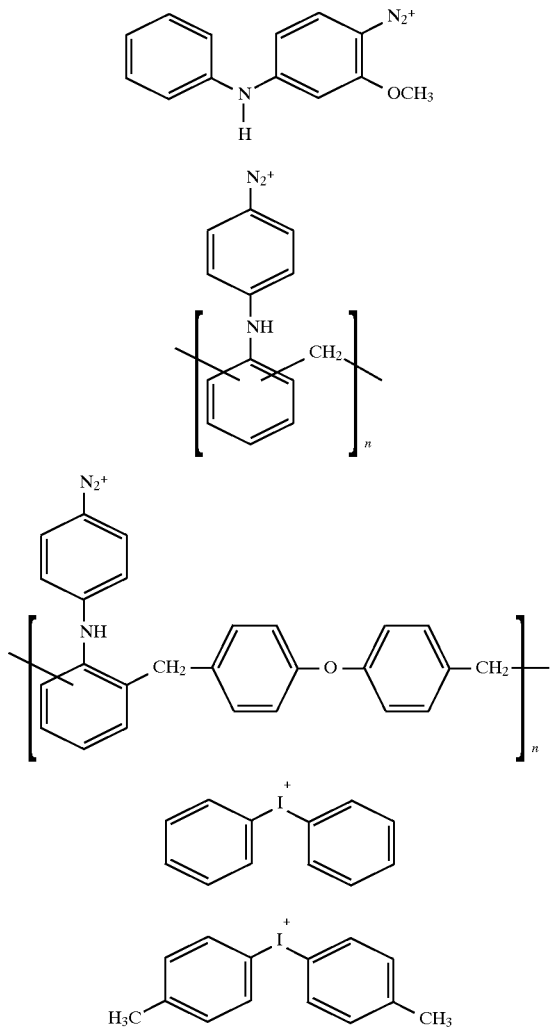

TABLE II-continued
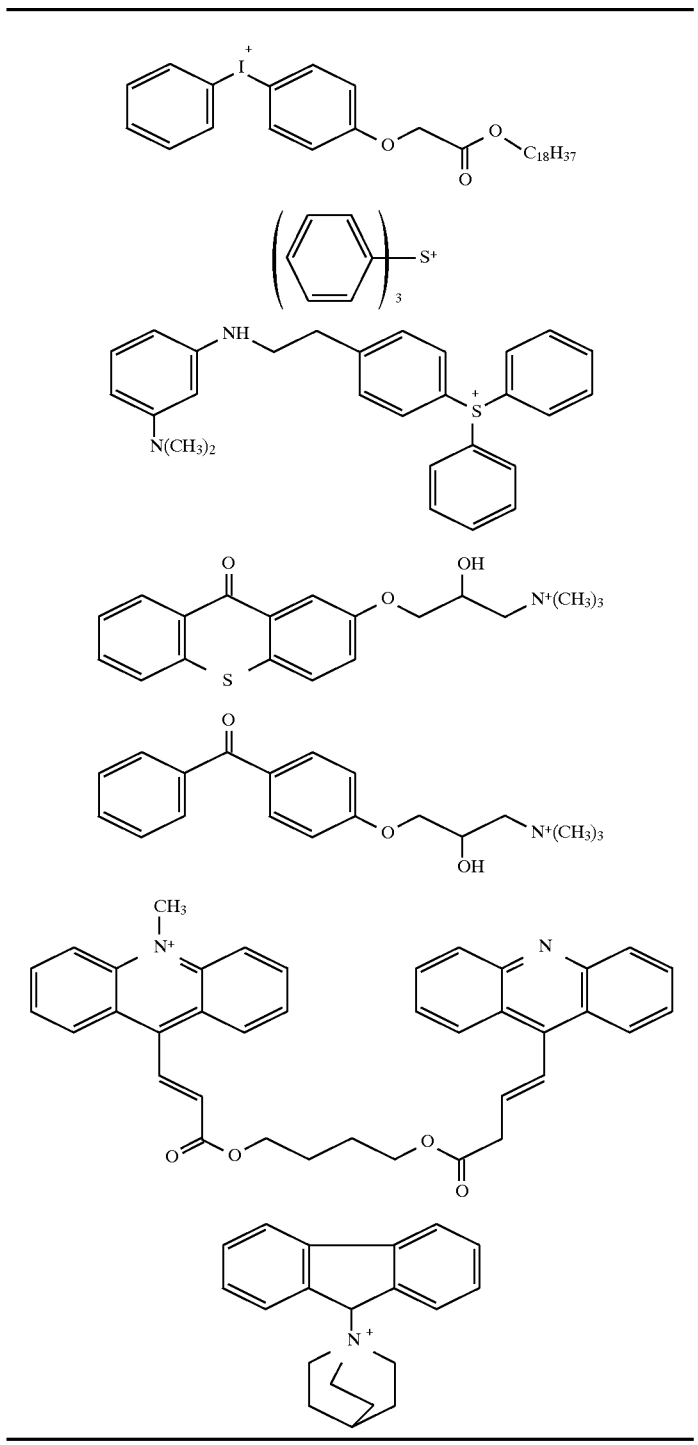
Representative examples of halomethyl,1,3,5-triazine anion (T⁻) which may used to produce ionic bifunctional photoinitiators (P⁺ T⁻) are listed in Table III.

TABLE III
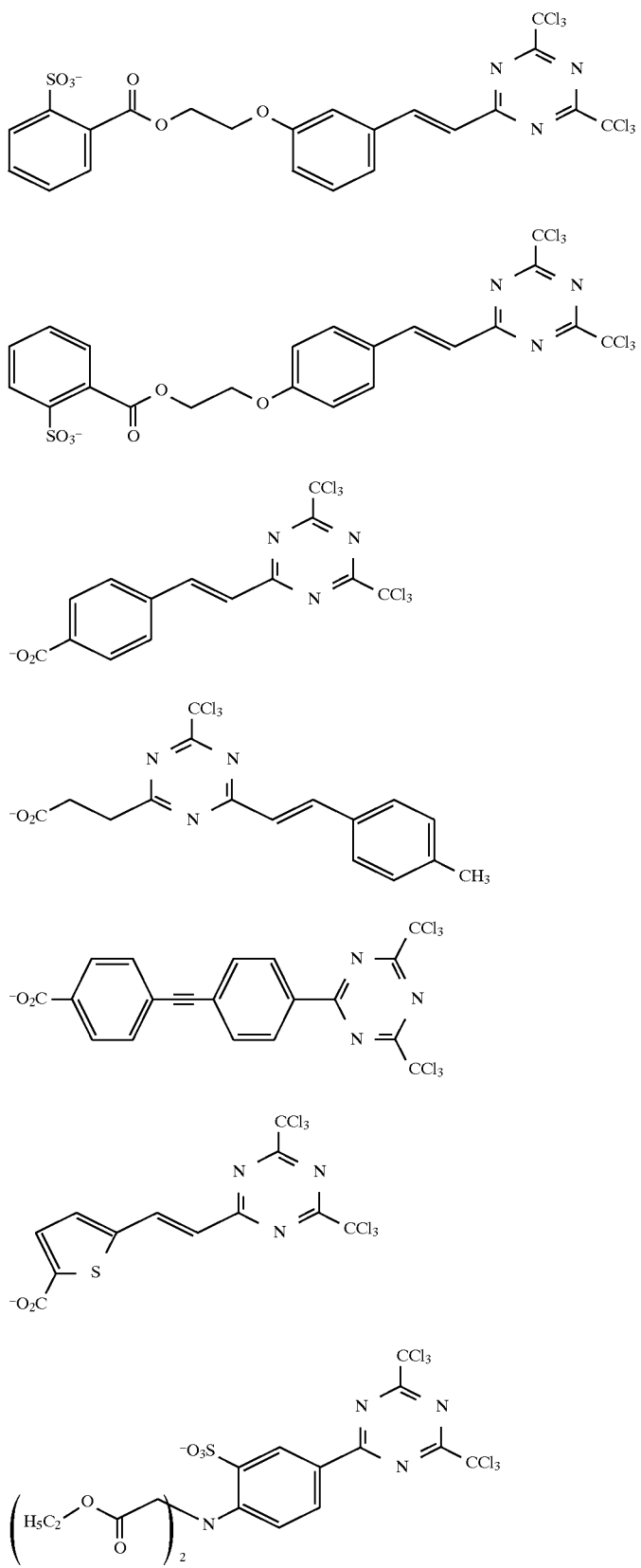

TABLE III-continued

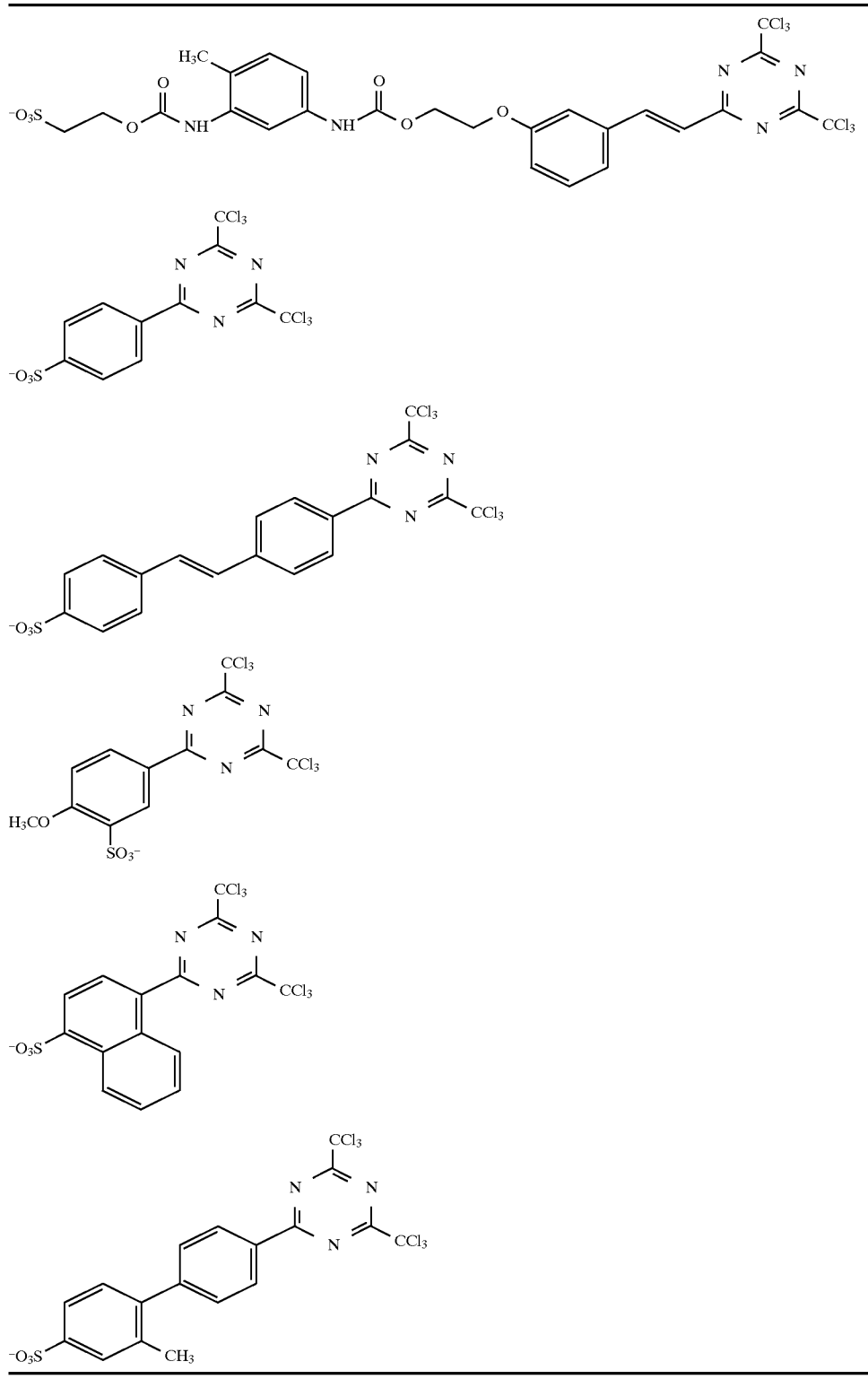

Compounds P⁺T⁻ are useful as photoinitiators in radiation sensitive compositions. In particular, the photoinitiators are useful for the in-situ photochemical production of free radical species or acidic species which are subsequently used to initiate free radical catalyzed polymerization, or acid catalyzed polymerization, or to react with acid sensitive compounds. Representative examples of acid sensitive compositions, in which the ionic bifunctional photoinitiators (P⁺T⁻) are useful as acid-generating photoinitiators, contain acid-cleavable compounds having C—O—C or C—O—Si bonds, as described in U.S. Pat. Nos. 3,779,778 and 5,364,734 incorporated herein by reference. Examples of radiation-sensitive compositions in which the ionic bifunctional photoinitiators ($P^+T^-$) can photoinitiate the acid-catalyzed insolubilization of resins are described in U.S. Pat. Nos. 5,466,557 and 5,494,777 incorporated herein by reference.

The sensitivity of compositions containing the ionic bifunctional photoinitiators ($P^+T^-$) to actinic radiation of a particular range of wavelengths can be increased by the incorporation of known ultraviolet and visible light sensitizers including cyanine, carbocyanine, merocyanine, stryryl, acridine, polycyclic aromatic hydrocarbons, polyarlyamines, and amino-substituted chalcones. Suitable cyanine dyes are described in U.S. Pat. No. 3,495,987. Suitable styryl dyes and polyarylamines are described in Kosar, *Light Sensitive Systems*, J. Wiley and Sons (New York, 1965), pp 361–369. Polycyclic aromatic hydrocarbons useful as sensitizers (i.e., 2-ethyl-9,10, dimethoxyanthracene) are described in U.S. Pat. No. 3,640,718. Amino substituted chalcones useful as sensitizers are described in U.S. Pat. No. 3,617,288. A wide variety of suitable sensitizing dyes are described in U.S. Pat. Nos. 4,069,054; 4,026,705 and 4,250,053. The ionic bifunctional photoinitiators ($P^+T^-$) can also be substituted for the triazines used in conjunction with dialkylamino aromatic carbonyl compounds described in U.S. Pat. No. 4,259,432; 2-(benzoylmethylene)-5-benzothiazolidene thiazole-4-1 compounds described in EP application 109,291; 3-keto-substituted coumarin compounds described in U.S. Pat. Nos. 4,505,793; 4,239,850 and 5,455,143.

Photopolymerizable compositions wherein the ionic bifunctional photoinitiators ($P^+T^-$) can be used as photoinitiators typically comprise an unsaturated, free radical initiated, chain propagating addition polymerizable compound, the ionic bifunctional photoinitiator ($P^+T^-$), and optionally one or more fillers, binders, dyes, polymerization inhibitors, color precursors, oxygen scavengers, etc. The ionic bifunctional photoinitiator ($P^+T^-$) should be present in an amount sufficient to initiate polymerization of the polymerizable compound. Examples of suitable ratios of ingredients are as follows: for every 100 parts of polymerizable compound there can be present from 0.005 to 10 parts of photoinitiator, from 0 to 200 parts of filler, from 0 to 200 parts of binder, and from 0 to 10 more parts of dyes, polymerization inhibitors, color precursors, oxygen scavengers, etc., as may be needed for a particular use of the photopolymerizable compositions. Preferably, there is used per 100 parts of polymerizable compounds 1 to 7.5 parts of the compound of this invention and from 25 to 150 parts of binder.

Unsaturated, free-radical initiated, chain-propagating addition polymerizable compounds suitable for use with the ionic bifunctional photoinitiator ($P^+T^-$) include mono- or multi-substituted alkylene or polyalkylene glycol (meth) acrylates, (i.e., ethylene glycol diacrylate, diethylene glycol diacrylate, glycerol diacrylate, glyerol triacrylate, ethylene glycol dimethacrylate, 1,3 propanediol dimethacrylate, 1,2, 4-butantetriol trimethacrylate, 1,4-cyclohexanediol diacrylate, pentaerythritol tetramethacrylate, pentaerythritol triacrylate, sorbitol hexacrylate; bis[1-(3-acryloxy-2-hydroxy)]-p-propoxyphenyl dimethylmethane, bis[1-(2-acryloxy)]-p-ethoxyphenyl)-dimethylmethane, tris hydroxyethylisocyanurate trimethacrylate, the bis-acrylate and the bis-methacrylates of polyethylene glycols of molecular weight between 200 and 500); unsaturated amides, (i.e., methylene bis-acrylamide, methylene bis-methacrylamide, 1,6-hexamethylene bis-acrylamide, diethylene triamine trisacrylamide, betz-methacrylaminoethylmethacrylate); vinyl esters (i.e., divinyl succinate, divinyl adipate, divinyl phthalate) and combinations thereof. Preferred unsaturated compounds include pentaerythritol tetracrylate, bis[p-(3-acryloxy-2-hydroxypropoxy)phenyl]-dimethylmethane, and bis[p-(2-acryloxyethoxy)phenyl]-dimethylthane. Mixtures of these esters can also be used with alkyl esters of (meth) acrylic acid, such as methyl (meth)acrylate, ethyl (meth) acrylate, isopropyl (meth)acrylate, n-hexyl acrylate, stearyl acrylate, allyl acrylate, diallyl phthalate, and combinations thereof.

Pigments or dyes may be added to the photopolymerizable composition to provide color. Pigments or polymeric dyes are preferred in color proofing elements since they have a lower tendency for migration between the layers. Pigments are more preferred due to the wide variety of colors available and lower cost. Pigments are generally introduced into the photopolymerizable composition in the form of a millbase comprising the pigment dispersed with a binder and suspended into a solvent or mixture of solvents. The dispersion process may be accomplished by a variety of methods well known in the art, such as two-roll milling, three-roll milling, sand milling, ball milling, etc. Many different pigments are available and are well known in the art. The pigment type and color are chosen such that the coated color proofing element is matched to a preset color target or specification set by the industry. Color enhancing additives may be used which include fluorescent, pearlescent, iridescent, and metallic materials. Materials such as silica, polymeric beads, reflective and non-reflective glass beads, or mica may also be added in place of a colorant to provide a textured image. The color enhancing additives or texturing materials may be used either alone or in combination with the above pigments to produce colored images with the desired visual effects.

The type of dispersing resin and the pigment to resin composition ratio chosen are dependent upon the pigment type, surface treatment on the pigment, dispersing solvent and milling process. Some examples of resins suitable for generating millbases which are compatible with the aforementioned photo-oligomers and monomers include; polyvinyl acetate/crotonic acid copolymers, styrene/maleic anhydride partial-ester resins, acid containing acrylic and methacrylic polymers and copolymers, polyvinyl acetals, polyvinyl acetals modified with anhydrides and amines, hydroxy alkyl cellulose resins and styrene/acrylic/acrylic acid resins. The dispersion may contain a mixture of these resins. The pigment to resin ratio in the dispersion is typically between 0.6 to 5.0, preferably between 0.8 to 3.0.

A dispersing agent may be necessary to achieve optimum dispersion quality. Some examples of dispersing agents include; polyester/polyamine copolymers, alkylarylpolyether alcohols, acrylic resins and Disperbyk™ wetting agents available from Byk-Chemie USA, Wallingford, Conn. Other components may also be included in the millbase such as surfactants to improve solution stability, fluorescent materials, optical brighteners, UV absorbers, fillers, etc.

Photosensitive compositions are prepared by simply mixing the desired components described above to form a solution or uniform dispersion. The photopolymerizable composition is then coated onto any suitable substrate using a variety of coating methods known to those skilled in the art. The substrate is chosen based on the particular applicaton (i.e., printing plates, color proofing films, printed circuit boards, etc.). Substrates may be transparent or opaque. Suitable substrates include, metals (i.e., steel, and aluminum plates including aluminum treated with hydrophilizing agents such as silicates or polyacrylic acid and its derivatives, sheets, and foils); films or plates composed of various film-forming synthetic or high polymers including addition polymers (e.g., poly(vinylidene chloride), poly (vinyl chloride), poly(vinyl acetate), polystyrene, polyisobutylene polymers and copolymers), and linear condensation polymers (e.g., poly(ethylene terephthalate), poly (hexamethylene adipate), and poly(hexamethylene adipamide/adipate)). Polyester substrates are generally preferred for color proofing applications and aluminum substrates are preferred for printing plate applications. Grained, anodized, and silicated aluminum is particularly preferred. The coated substrates are maintained in the absence of light unless the element is sensitized to a narrow range of the electromagnetic spectrum outside the range of normal light and the element is provided with a filter layer which excludes normal visible light.

The photosensitive element is exposed through a separation negative and developed to form an image. In the imaging process, the spectral and power output of the exposure unit and the absorption of the photoinitiator system are chosen for an optimum exposure speed. Typical exposure units are equipped with UV lamps having optimum spectral outputs between 250 nm and 500 nm and a power output between 2.5 and 10 Kilowatts.

Developer solutions used to develop the image after exposure are typically comprised of a combination of sodium or potassium carbonate, and sodium or potassium bicarbonate and a surfactant. In a preferred developer solution, the carbonate is present at about 0.5–2.0% by weight, the bicarbonate is present at about 0–1.0% by weight, and the surfactant is present at about 0.1–1.0% by weight of the total aqueous developer solution. Preferred surfactants include; Surfynol™ 465 (ethoxylated tetramethyl decynediol, available from Air Products and Chemicals, Allentown, Pa.), Surfactol™ 365 (ethoxylated castor oil, available from CasChem Inc., Bayonne, N.J.), Triton™ X-100 (octylphenoxypolyethoxyethanol, available from Rohm and Haas, Philadelphia, Pa.), and Surfynol™ GA (acetylenic diols compounded with other non-ionic surfactants and solvents, available from Air Products and Chemicals, Allentown, Pa.).

Objects and advantages of the invention are further illustrated by the following examples, but the particular materials and amounts recited in these examples, as well as other conditions and details, should not be construed to unduly limit the invention.

EXAMPLES 1–2

Examples 1 and 2 illustrate the preparation of water soluble halomethyl-1,3,5-triazine compounds containing a sulfonic acid group by a reaction of 2-sulfobenzoic anhydride with a hydroxyl substituted trichloromethyltriazine compound.

Example 1

Example 1 describes the preparation of the following Compound A:

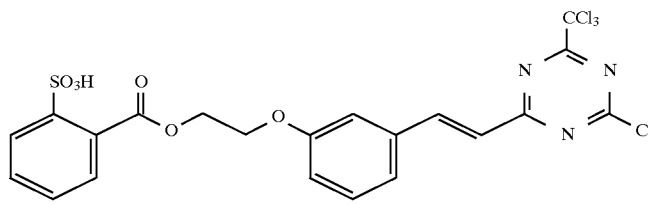

Compound A

A slurry of 216.5 g (0.0.453 eq) of 2,4-bis (trichloromethyl)-6-[3-(2-hydroxyethoxy)styryl]-1,3,5-triazine in 1400 mL of toluene was prepared and the water impurity was removed by azeotropic distillation of approximately 100 ml of the solvent. After cooling to room temperature, 100 g (0.543 eq) of 2-sulfobenzoic acid anhydride (Aldrich Chemical) was added. The solution was heated to 70° C. and the reaction was complete in about 3 hrs. as determined by FTIR and TLC. After cooling to room temperature, the reaction solution was filtered to remove a small amount of a brown impurity. The filtrate was then slowly poured into a solution of 5000 mL heptane/1000 mL 2-propanol with rapid stirring at 10° C. The product precipitated and was collected by filtration. A rubber dam was used during the filtration to help remove excess solvent. After drying at 50°–60° C., 247.5 g (83% yield) of a slightly yellow, deliquescent solid was collected. The product dissolved in water at a concentration of at least 10%, and was very soluble in a wide variety of organic solvents such as methanol, acetone, ethyl acetate, chloroform, and toluene. The structural formula of the product was confirmed by NMR and FTIR to be the trichloromethyltriazine compound with a sulfonic acid group illustrated above as Compound A.

Example 2

Example 2 describes the preparation of the following Compound B:

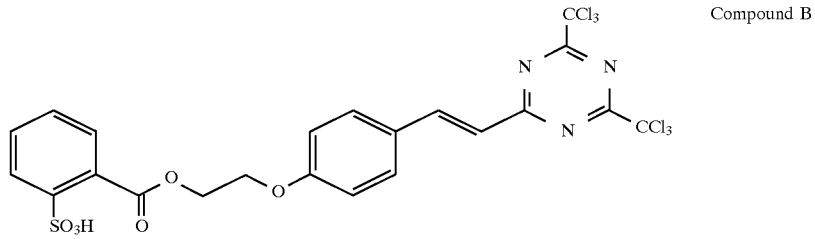

Compound B

Compound B

The procedure of Example 1 was repeated with the exception being that 2,4-bis(trichloromethyl)-6-[4-(2-hydroxyethoxy)styryl]-1,3,5-triazine was used instead of 2,4-bis(trichloromethyl)-6-[3-(2-hydroxyethoxy)styryl]-1,3,5-triazine.

EXAMPLES 3–5

Examples 3–5 illustrate the preparation of compounds of general Formula I by reacting diazonium salts with halomethyl-1,3,5-triazine compounds substituted with a sulfonic acid group.

Example 3

Example 3 describes the preparation of Compound C by reacting a diazonium resin salt with Compound A of Example 1 and dodecylbenzene sulfonic acid.

filtration. The wet precipitate was washed two times by slurrying it in 3000 mL of deionized water and filtering. After tray drying at room temperature for 24 hrs., 61 g (theoretical yield is 60 g) of the diazonium resin salt product was collected as a light brown powder. The FTIR and NMR confirm the presence of the sulfonate anion of the halomethyl-1,3,5-triazine. The product is soluble in methyl ethyl ketone.

Example 4

Example 4 describes the preparation of Compound D by reacting a diazonium resin salt with Compound A of Example 1 and mesitylene sulfonic acid.

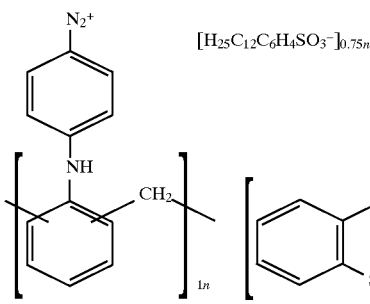
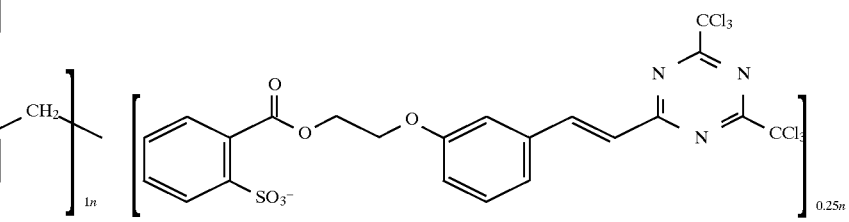

Compound C

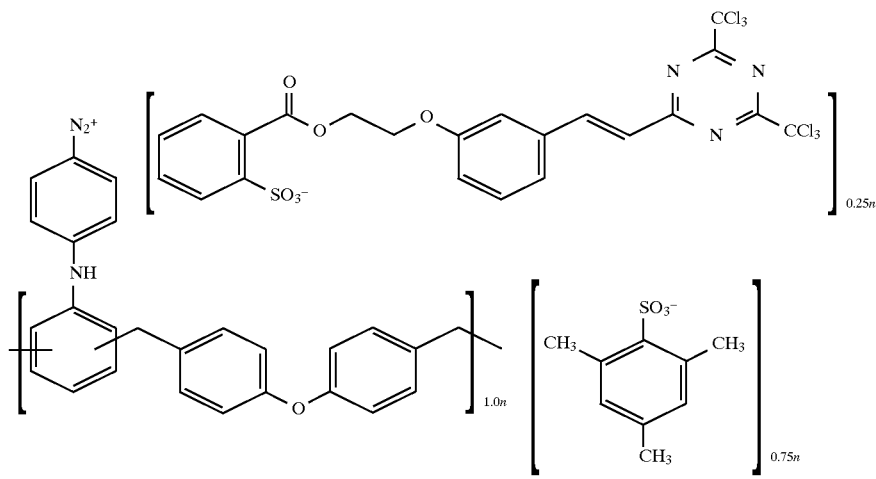

Compound D

Compound C

A solution of 32.20 g (0.10 eq) of a diazonium resin (which is the zinc chloride salt of the condensation product of 4-azodiphenylamine with formaldehyde) in 800 mL of deionized water was added slowly (ca. 30 min) with stirring to a solution of 18.25 g (0.028 eq) of the trichloromethyl-triazine sulfonic acid (Compound A of Example 1) and 28.75 g (0.082 eq) of dodecylbenzene sulfonic acid (Aldrich Chemical) in 2200 mL of deionized water. After stirring an additional 30 min., a fine tan precipitate was collected by

Compound D

To a solution of 5.15 g (0.01 eq) of a diazonium resin [Hoechst 1769 available from Focus Chemical, which is the methane sulfonate salt of the condensation product of 4,4'-bis-(methoxymethyl)diphenyl ether) and 4-azodiphenylamine] in 200 mL of deionized water was added slowly with stirring a solution of 1.65 g (0.0025 eq) of the trichloromethyltriazine sulfonic acid (Compound A of Example 1) and 1.50 g (0.0075 eq) of mesitylene sulfonic acid (Aldrich Chemical) in 150 mL of deionized water. A yellow product precipitated which was isolated by filtration, washed with deionized water, and allowed to dry at ambient temperature. The product was shown by FTIR analysis to be a mixed salt of the diazonium resin, the trichloromethyltriazine sulfonate, and mesitylene sulfonate consistent with the structural formula for Compound D illustrated above.

Example 5

Example 5 describes the preparation of Compound E by reacting a diazonium salt with Compound A of Example 1.

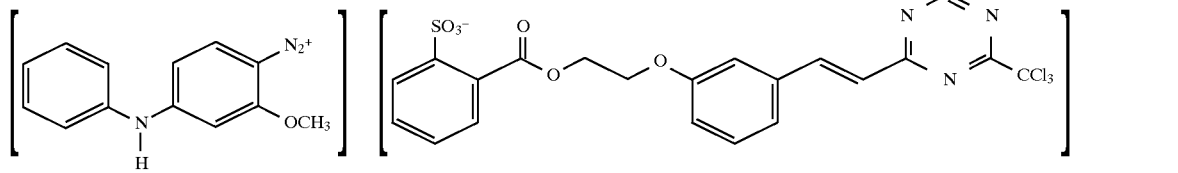

Compound E

A solution of 3.23 g of the trichloromethyltriazine sulfonic acid (Compound A of Example 1) in 100 mL of deionized water was added slowly with stirring to a solution of 6.62 g of 4-diazo-2-methoxydiphenyl amine hydrogen sulfate in 100 mL of deionized water. A bright yellow precipitate formed which was collected by filtration, washed with deionized water and dried overnight at room temperature. A yellow powder, 6.90 g, was isolated and shown by FTIR and NMR to contain greater than 97% of the salt of a diazonium cation and a trichloromethyltriazine sulfonate anion having the structural formula consistent with Compound E illustrated above.

Example 6

Example 6 describes the preparation of Compound F by reacting diphenyliodonium chloride with Compound A of Example 1.

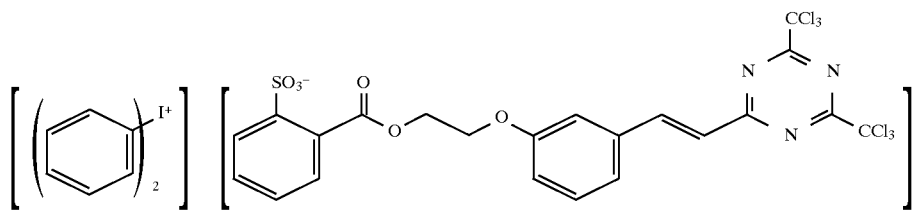

Compound F

A solution of 3.16 (0.01 eq) of diphenyliodonium chloride in 100 mL of deionized water and 10 mL of methanol (slight heating required to dissolve) wwas added slowly with stirring to a solution of 6.62 g of the trichloromethyltriazine sulfonic acid (Compound A of Example 1) in 200 mL of deionized water. To the milky suspension was added about 50 mL of saturated sodium chloride and a white precipitate was formed, which was isolated by filtration and washed with deionized water. After drying, 8.1 g of a white solid was collected, mp. 189°–191° C. and shown by NMR and FTIR to be the iodonium salt of the trichlormethyltriazine sulfonate having the structural formula consistent with Compound F illustrated above.

Example 7

Example 7 describes the preparation of Compound G by reacting a triphenylsulfonium hexafluorophosphate with Compound A of Example 1.

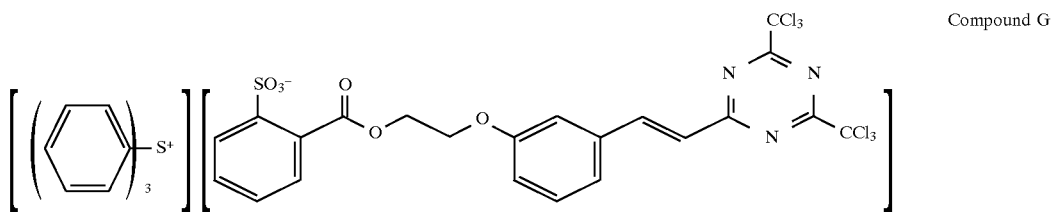

Compound G

A solution of 2.21 g of impure triphenylsulfonium hexafluorophosphate in 50 mL of acetone was mixed with a solution of 2.30 g of the trichloromethyltriazine sulfonic acid (Compound A of Example 1) in 50 mL of acetone. Upon the addition of 100 mL of deionized water, a milkly solution was formed, to which about 50 mL of saturated sodium chloride was then added. The resulting precipitate was isolated by filtration, washed with deionized water, and dried to give 4.0 g of a white solid. This solid was observed by NMR to contain small amounts of the unknown impurity originally present in the sulfonium starting material. The purity of the desired sulfonium/triazine sulfonate salt is greater than 97% and has the structural formula consistent with Compound G illustrated above.

EXAMPLES 8 –10

Examples 8–10 describe the preparation of compound of General Formula I by reacting a photoinitiator having a quaternary ammonium group with a halomethyl-1,3,5-triazine compound containing a sulfonic acid group.

Example 8

Example 8 describes the preparation Compound H by reacting a thioxanthone photoinitiator substituted with a quaternary ammonium group with the Compound A of Example 1.

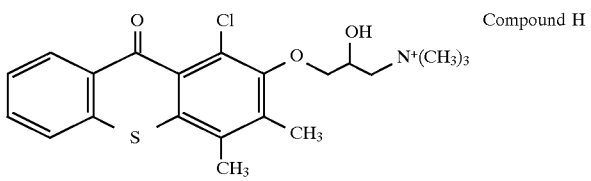

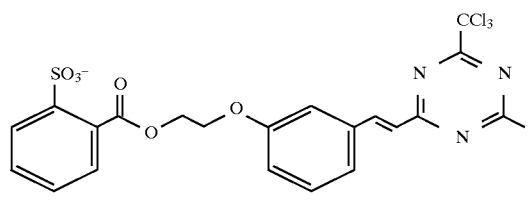

Compound H

A solution of 4.08 g (0.01 eq) of 2-hydroxy-3-(1-chloro-3,4-dimethyl-9-oxo-9H-thioxanthen-2-yloxy)-N,N,N-trimethylpropanaminium (Quantacure QTX, Octel Chemcals) in 100 mL of deionized water was added slowly to a stirred solution of 6.62 g (0.01 eq) of the trichloromethyltriazine sulfonic acid (Compound A of Example 1). A finely divided precipitate was formed which was isolated by filtration. The moist cake was slurried in 200 mL of 2-propanol, filtered, and dried to give 7.2 g of a slightly yellow solid, which was shown by FTIR, UV/VIS, and NMR to contain greater than 98% of the quaternary ammonium sulfonate salt having the structural formula consistent with Compound H illustrated above.

Example 9

Example 9 describes the preparation of Compound I by reacting a thioxanthone photoinitiator substituted with a quaternary ammonium group with the Compound B of Example 2.

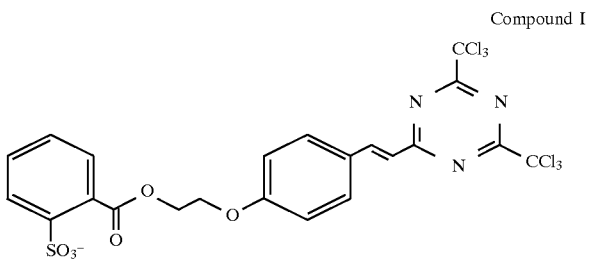

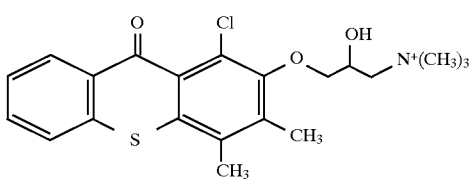

Compound I

A solution of 1.02 g (0.0025 eq) of 2-hydroxy-3-(1-chloro-3,4-dimethyl-9-oxo-9H-thioxanthen-2-yloxy)-N,N,N-trimethylpropanaminium (Quantacure™ QTX, Octel Chemcals) in 100 mL of deionized water was added slowly to a stirred solution of 1.65 g (0.0025 eq) of the trichloromethyltriazine sulfonic acid (Compound B of Example 2). A finely divided precipitate was formed which was isolated by filtration. The moist cake was slurried in 100 mL of 2-propanol, filtered, and dried to give 1.30 g of a slightly yellow solid, which was shown by FTIR, UV/VIS, and NMR to contain greater than 98.5% of the quaternary ammonium sulfonate salt having the structural formula consistent with Compound I illustrated above.

Example 10

Example 10 describes the preparation Compound J by reacting a benzophenone photoinitiator substituted with a quaternary ammonium group with the Compound A of Example 1.

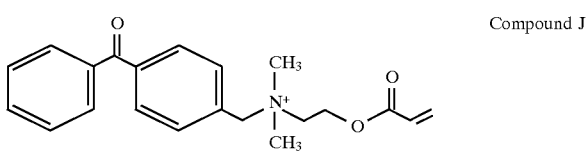

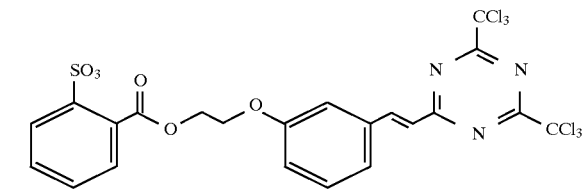

Compound J

A solution of 6.62 g (0.01 eq) of the trichloromethyltriazine sulfonic acid (Compound A of Example 1) in 200 mL of deionized water was added slowly with stirring to a solution of 4.18 g (0.01 eq) of 4-benzoyl-N,N-dimethyl-[2-(1-oxo-2-propenyloxy)ethyl]benzene-methanaminium bromide (Quantacure ABQ, Octel Chemicals) in 150 mL of deionized water. After stirring the milky solution for 30 min., a tacky ball formed which was isolated by decanting the liquid portion. The wet precipitate was dissolved in 100 mL of methylene chloride and the solution treated with anhydrous sodium sulfate. After removing the sodium sulfate by filtration, hexane was added to the filtrate to form a taffy-like solid. This material was redissolved in methylene chloride and reconcentrated on a rotary evaporator to give 5 g of a dry, white solid, which was shown by FTIR and NMR to contain greater than 97% of the ammonium sufonate salt having the structural formula consistent with Compound J illustrated above.

EXAMPLES 11–14

Examples 11–14 demonstrate the use of ionic bifunctional photoinitiators in photosensitive compositions applied in a variety of imaging element constructions.

Preparations

The following preparations describe methods for preparing materials or solutions referred to in the Examples 11–14 that were not acquired through a commercial source or described earlier in Examples 1–10. All commercial materials are available from Aldrich Chemical (Milwaukee, Wis.), unless designated otherwise.

Polyvinylacetal resin PVA-1:

Polyvinyl acetal resin PVA-1 was prepared by reacting in a closed vessel 1.0 eq of a polyvinyl alcohol resin that was approximately 88% hydrolyzed (Airvol™ 203, Air Products and Chemicals, Inc.) with 0.25 eq of 2-carboxybenzaldehyde and 0.53 eq. of 4-isopropylbenzaldehyde at a concentration of about 12.5 % in 2:1 1-propanol/water containing conc. HCl at a concentration of 1.7% at 60° C. for 10 hours. The polyvinyl acetal resin was isolated by pouring the reaction solution into water with rapid stirring and heating in an oven at 40° C. until dry.

Acrylated Polymer A-1:

Acrylated acrylic resin B-1, having pendent acrylamide groups, was prepared by reacting approximately 0.5 to 0.6 eq. of the acid groups of polyacrylic acid with 2-isocyanatoethyl methacrylate.

Acidified Butvar™ B-98:

A 2 liter 3-necked roundbottom flask equipped with an overhead stirrer was charged with 300 g of Butvar™ B-98 (available from Monsanto Co., St. Louis, Mo.), 90 g of succinic anhydride, 90 g of triethylamine and 900 g of methyl ethyl ketone. The mixture was heated at 77° C. for six hours. The solvent was removed under vacuum yielding a white solid. An Infrared spectrum of the material showed no anhydride peaks.

Acrylated Urethane Oligomer P-11: (as described in U.S. Pat. No. 4,304,923)

Polycaprolactone hexol was prepared by adding 63.5 g dipentaerythritol, 228 g of epsilon-caprolactone, and 0.02 g of 2,6-di-t-butyl-4-methylphenol to a 500 mL, three-neck flask equipped with an overhead mechanical stirrer and a condenser. The liquid was deoxygenated for 20 minutes by bubbling with dry nitrogen from a gas dispersion tub. This tube was then replaced with a gas inlet adapter and the reaction mixture heated while maintaining a slight positive pressure with nitrogen. The mixture was maintained at 170° C. for 5 hours under continual stirring. The reaction mixture was then allowed to cool to room temperature under nitrogen atmosphere.

A 1 liter three-neck flask was fitted with an adapter, mechanical stirrer, thermometer, addition funnel and drying tube. To this flask was charged 175 g of the polycaprolactone hexol and 60 mL of methyl ethyl ketone. A solution of 13 g of 2,4-tolylene diisocyanate in 9 mL of methyl ethyl ketone was slowly dripped into the first solution with stirring at room temperature. The addition was completed in 20 minutes and the reaction mixture stirred for 90 minutes at 30° C.

To a second flask fitted with an overhead mechanical stirrer, thermometer, addition funnel and drying tube was charged 86.1 g of 2,4-tolylene diisocyanate. Through the addition funnel was added 70.2 g of 2-hydroxyethylmethacrylate (herein after refered to as "HEMA") and 0.02 g of 2,6-di-t-butyl-4-methylphenol (herein after refered to as "inhibitor") slowly with stirring to the diisocyanate while maintained below or at 30° C. The addition was completed in 15 minutes and after 40 minutes of reaction time, a white solid formed. The solid was dissolved in 45 mL of methyl ethyl ketone by heating to 45° C. and held at that temperature for 10 minutes to complete the reaction.

The flask containing the reaction product of the polycaprolactone hexol and the 2,4-tolylene diisocyanate was heated to 67° C. and the solution of the HEMA/2,4-tolylene diisocyanate adduct in methyl ethyl ketone was added slowly with stirring over a period of 2 hours. 27 g of succinic anhydride was then added with an additional 0.02 g of the inhibitor. Heating and stirring was continued until the anhydride had completely reacted (about 5–6 hours).

Blue Millbase BM-1:

A 20% by weight dispersion was prepared by dispersing 5 parts by weight Sunfast Blue 249-1284 pigment (available from Sun Chemical Corp.) and 1 part by weight vinylchloride/vinyl acetate copolymer ("VYNS-3" resin, Union Carbide Corp.) in methyl ethyl ketone.

Black Millbase and Cyan Millbase:

The black and cyan millbases used in Example 12 were prepared by dispersing the following ingredients.

| Ingredients | Black Millbase | Cyan Millbase |
|---|---|---|
| Raven ™ 760 (Black pigment, available from Columbian Chemicals Co., Tulsa, OK) | 332.2 g | — |
| Sun 248-0615 Red Shade Cyan (available from Sun Chemical, Cincinnati, OH) | — | 872.1 g |
| Butvar ™ B-98 (Polyvinyl butyral resin available from Monsanto Co., St. Louis, MO) | 59.3 g | 290.7 g |
| Joncryl ™ 67 (styrene/acrylic resin, available from S. C. Johnson Wax, Racine, WI) | 177.7 g | 290.7 g |
| Disperbyk ™ 161 (available from Byk-Chemie USA, Wallingford, CT) | 29.7 g | 43.6 g |
| FC-430 (fluorchemical surfactant, available from 3M, St. Paul, MN) | 1.1 g | 3.3 g |
| 1-methoxy-2-propanol | 3000.0 g | 1500.0 g |

Oxygen Barrier Coating Solution:

The oxygen barrier coating solution used in Examples 12–14 was prepared by dissolving the following ingredients.

| | |
|---|---|
| Airvol ™ 540 Polyvinyl alcohol (available from Air Products and Chemicals, Allentown, PA) | 843 g |
| Airvol ™ 205 Polyvinyl alcohol (available from Air Products and Chemicals, Allentown, PA) | 2,458 g |
| PVP K-90 (polyvinyl pyrolidone, available from GAF Chemical Corporation, Wayne, NJ) | 2,298 g |
| Kathon ™ CG/ICP Preservative (available from Rohm and Haas, Philadelphia, PA) | 5.8 g |
| Stearyl methacrylate/hexanediol diacrylate Beads | 15.0 g |
| Deionized Water | 11,379 g |

Example 11

Example 11 describes the preparation of a radiation-sensitive composition and lithographic printing plate using Compound C prepared in Example 3.

A radiation-sensitive solution having the following ingredients in the corresponding amounts was prepared by pre-dissolving the polyvinyl acetal resin in the dimethylacetamide and adding it to a solution of the other ingredients.

| Ingredients | Amount |
|---|---|
| Polyvinyl acetal resin PVA-1 | 0.188 g |
| Compound C of Example 3 | 0.563 g |
| Acrylated polymer A-1 | 0.938 g |
| 4-phenylazodiphenylamine | 0.0 g |
| Blue Millbase BM-1 | 0.188 g |
| 1-methoxy-2-propanol | 20.300 g |
| Dimethylacetamide | 1.700 g |
| Water | 0.125 g |

A lithographic plate was prepared by coating the solution onto an aluminum sheet (previously electrochemically grained, anodized, and silicated) with a wire wound rod and removing the solvent in a heated air oven. The resultant dried photosensitive layer had a coating weight of approximately 0.100 g/ft². The plate was imaged by exposing the photosensitive layer through a 41-step photographic step wedge for 24 seconds using a Berkey® vacuum exposure frame fitted with a 5 Kw diazo bulb. The aluminum plate was then passed through an automatic processor (Model 1133 Viking™ plate processor available from Imation™ Corp, Oakdale, Minn.) containing an aqueous developer (Viking™ negative developer available from Imation™ Corp). Approximately 21 steps were reproduced in the photographic step-wedge. The plates produced high quality halftone prints and had a good press life.

Examples 12–14

Examples 12, 13, and 14 describe the preparation of a pigmented photopolymerizable coating layer on a polyester film and illustrate the use of Compounds E, J and F prepared in Example 5, Example 10, and Example 6, respectfully, as a photopolymerization initiator.

Example 12

The following stock solution was prepared by combining the ingredients listed below in the respective amounts:

| | |
|---|---|
| Black Millbase | 39.00 g |
| Cyan Millbase | 7.43 g |
| Acidified Butvar ™ B-98 | 1.45 g |
| Joncryl ™ 67 Styrene-acrylic resin | 0.29 g |
| Echo ™ 310 (novolac diacrylate resin, available from Echo Resins and Laboratory, Versailles, MO) | 1.89 g |
| Acrylated Urethane Oligomer P-11 | 7.53 g |
| Methyl ethyl ketone | 106.65 g |
| 1-methoxy-2-propanol | 28.82 g |

A black photopolymerizable coating solution was then prepared by dissolving 0.15 g of Compound E of Example 5 in 10.00 g of the stock solution described above. This mixture was coated onto a 2.65 mil (0.07 mm) polyester film using a #6 wire-wound rod and dried for 2 minutes at 200° F. (93° C.) for 2 min. The black photopolymerizable layer was then overcoated with the oxygen barrier coating solution described above using a #4 wire-wound rod and dried at 200° F. (93° C.) for 2 minutes.

The radiation sensitive coating was exposed for 25 units under vacuum using an UGRA plate control test target (available from EMPA/Urga, St. Gallen, Switzerland) with a UV light source having a power output of 0.15 Watt/cm2. The image was developed using a buffered aqueous solution containing 1% potassium carbonate, 1% potassium bicarbonate, and 0.1% ethoxylated tetramethyldecynediol surfactant (Surfynol™ 465, available from Air Products and Chemicals, Allentown, Pa.), in water. The resultant image reproduced 3.5 steps of the photographic wedge and resolved 1% highlight halftone dots and 99% shadow halftone screens.

Example 13

The procedure of Example 12 was repeated with the exception that Compound J of Example 10 was used instead of Compound E of Example 5 and that the exposure was not done under vacuum. The resultant image was of good quality and 5 steps of the photographic step-wedge were reproduced.

Example 14

A black photopolymerizable coating solution was prepared by combining the following ingredients listed below in the respective amounts at a concentration of 11% by weight in a solvent mixture of 70/30 methyl ethyl ketone/1methoxy-2-propanol:

| | |
|---|---|
| Acrylated Urethane Oligomer P-11 | 35.00 g |
| Acidified Butvar ™ B-98 | 5.00 g |
| Butvar ™ B-98 | 3.89 g |
| 2-ethyl-9,10-dimethoxyanthracene | 5.00 g |
| Joncryl ™ 690 Styrene-acrylic resin (available from S. C. Johnson Wax, Racine, WI) | 20.34 g |
| Raven ™ 760 Black Pigment | 18.71 g |
| Disperbyk ™ K-161 | 1.58 g |
| FC-430 Fluorocarbon surfactant | 0.47 g |
| Compound F of Example 6 | 10.00 g |

The photopolymerizable coating solution was coated onto polyester film, imaged and developed using the same procedures described in Example 12, with the exception that the exposure time was 120 units. The developed image reproduced 7.5 steps of the photographic wedge, 1% highlight halftone dots, and 99% shadow halftone screens.

Reasonable variations and modifications are possible from the foregoing disclosure without departing from either the spirit or scope of the invention as claimed.

What is claimed:

1. An ionic bifunctional photoinitiator having the structure:

$P^+ T^-$ wherein $P^+$ is a radiation-sensitive onium organic cation and $T^-$ is a halomethyl-1,3,5-triazine anion, said anion having a 1,3,5-triazine nucleus with at least one trihalomethyl group covalently attached to a carbon atom of said 1,3,5-triazine nucleus and a linking group covalently attached to both a second carbon atom of said 1,3,5-triazine nucleus and an anionic group.

2. The photoinitiator of claim 1 wherein said radiation-sensitive organic cation comprises an organic compound having at least one cationic substituent, said cationic substituent is selected from the group consisting of diazonium cations, iodonium cations, sulfonium cations, selenonium cations, arsonium cations, ammonium cations, and phosphonium cations.

3. The photoinitiator of claim 1 wherein said radiation-sensitive organic cation comprises a radiation-sensitive compound substituted with a cationic group selected from the group consisting of quaternary ammonium groups or quaternary phosphonium groups.

4. The photoinitiator of claim 3 wherein said radiation-sensitive compound is selected from the group consisting of benzoins, benzoin alkylethers, quinones, bis-imidazoles, acetophenones, and benzophenones.

5. The photoinitiator of claim 1 wherein said anionic group is selected from the group consisting of carboxyl anions, sulfonate anions, and phosphonate anions.

6. The photoinitiator of claim 1 wherein said linking group is selected from the group consisting of carbamato, carbamido, amino, amido, alkyl having 1 to 15 carbon atoms, oxy, alkenyl, alkynyl, keto, ester, sulfonyl, aryl, and combinations thereof.

7. The photoinitiator of claim 1 wherein said at least one trihalomethyl group is selected from the group consisting of trichloromethyl and tribromomethyl.

8. The photoinitiator of claim 1 wherein said halomethyl-1,3,5-triazine anion is represented by the general structure:

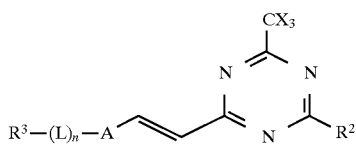

wherein

X is chlorine or bromine;

A is an aryl group having 1 to 3 rings;

L is a linking group selected from the group consisting of carbamato, carbamido, amino, amido, alkyl having up to 15 carbon atoms, oxy, alkenyl, alkynyl, keto, ester, sulfonyl, aryl, and combinations thereof; and n is 0 or 1;

$R^3$ is an acid anion selected from the group consisting of sulfonate, carboxylate, and phosphonate anions; and $R^2$ is —$CX_3$, —$NH_2$, NHR, —$NR_2$, —OR, or —R, where R is selected from the group consisting of an alkyl group having up to 15 carbon atoms, an aryl group having up to three rings, a heterocyclic aromatic group, and combinations thereof.

9. The photoinitiator of claim 1 wherein said halomethyl-1,3,5-triazine anion is selected from the group consisting of

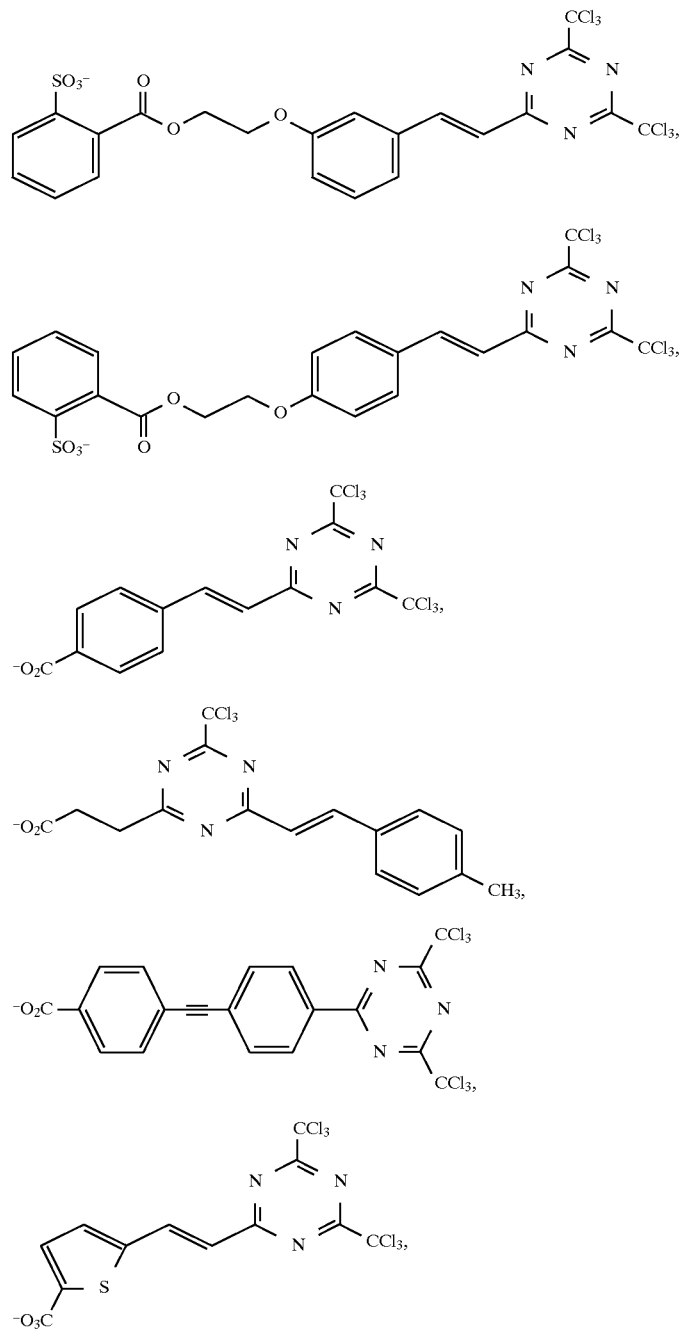

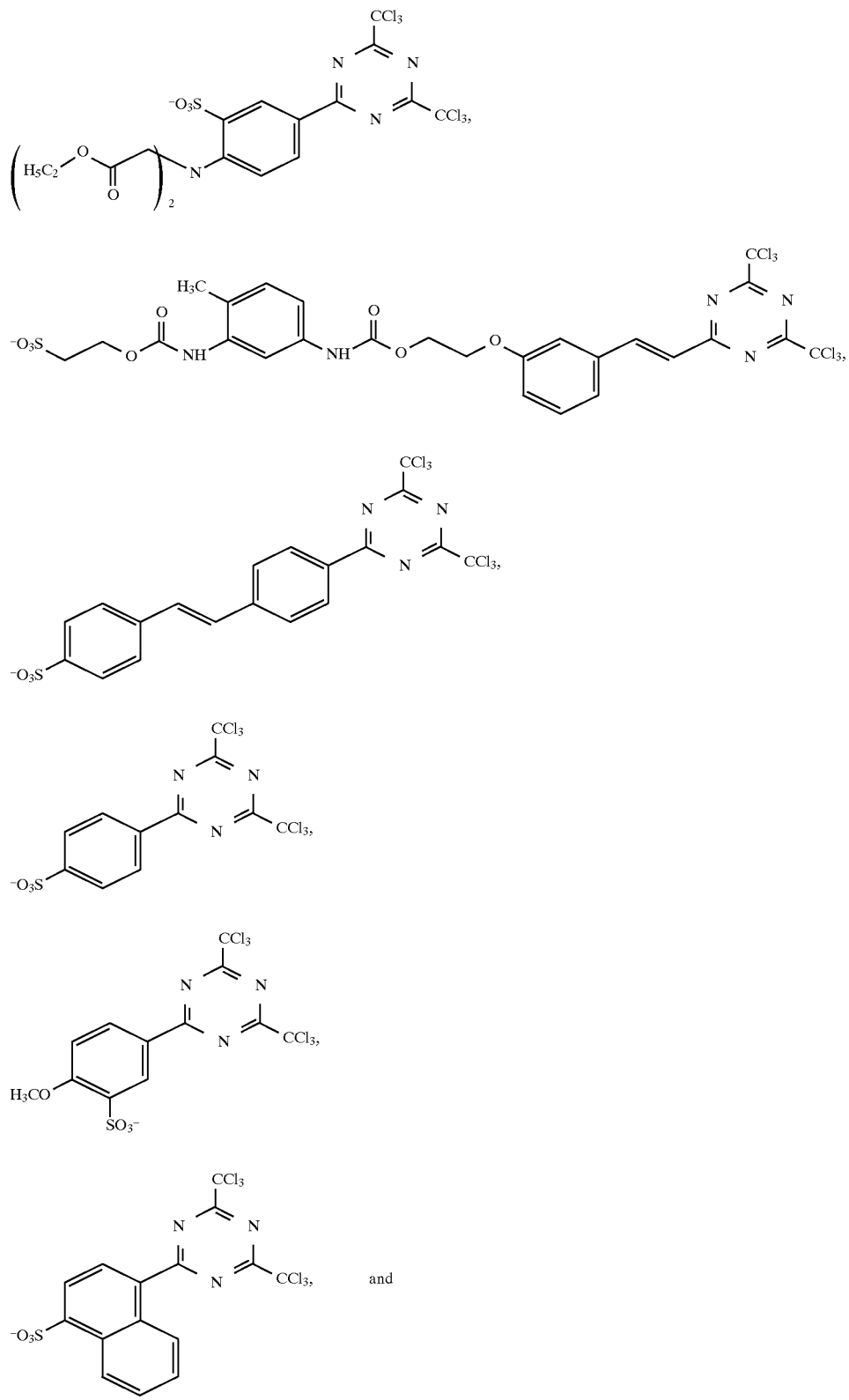

-continued

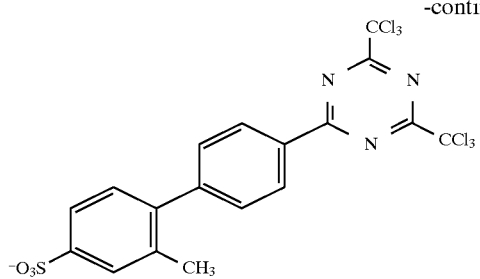

10. A process for preparing an ionic bifunctional photoinitiator of comprising the steps of:
   (a) providing a salt $P^+X^-$ in a solvent, wherein $P^+$ is a radiation-sensitive onium organic cation and $X^-$ is an inorganic anion;
   (b) providing a salt $M^+T^-$ in a second solvent, wherein $M^+$ is selected from the group consisting of a hydrogen proton, an organic cation, or an alkali metal cation, and
   $T^-$ is a halomethyl 1,3,5-triazine anion, said anion having a 1,3,5-triazine nucleus with at least one trihalomethyl group covalently attached to a carbon atom of said 1,3,5-triazine nucleus and a linking group covalently attached to both a second carbon atom of said 1,3,5-triazine nucleus and an anionic group;
   (c) mixing said salt $P^+X^-$ with said salt $M+T^-$ to provide said ionic bifunctional photoinitiator represented by the general formula $P^+T^-$.

11. The process of claim 10 wherein said solvent and said second solvent may be the same or different and are selected from the group consisting of water, alcohols, esters, amides, lactones, ethers, chlorinated hydrocarbons, aromatic hydrocarbons, ketones and combination thereof.

* * * * *